United States Patent [19]
Smith et al.

[11] Patent Number: 4,994,021
[45] Date of Patent: Feb. 19, 1991

[54] APPARATUS AND METHOD FOR COLLECTING AND FREEZING BLOOD PLASMA

[75] Inventors: Sidney T. Smith, Lake Forest; Dean M. Glash, McHenry, both of Ill.

[73] Assignee: Baxter International Inc., Deerfield, Ill.

[21] Appl. No.: 271,471

[22] Filed: Nov. 15, 1988

[51] Int. Cl.⁵ ............................................... A61J 1/00
[52] U.S. Cl. ........................................ 604/6; 604/409
[58] Field of Search .................... 604/6, 262, 408–410; 128/DIG. 24

[56] References Cited

U.S. PATENT DOCUMENTS

| 3,042,086 | 7/1962 | Winchell | 604/408 X |
| 3,722,557 | 3/1973 | Huggins | 141/314 X |
| 4,060,107 | 11/1977 | Naftulin | 141/114 |
| 4,253,458 | 3/1981 | Bacehowski et al. | 604/410 X |
| 4,253,458 | 3/1981 | Bacehowski et al. | 128/272 |
| 4,322,298 | 3/1982 | Persidsky | 604/6 X |
| 4,340,152 | 7/1982 | Ekholm, Jr. | 222/1 |
| 4,720,284 | 1/1988 | McCarty | 604/410 |

FOREIGN PATENT DOCUMENTS 2141723 7/1982 United Kingdom .

Primary Examiner—C. Fred Rosebaum
Assistant Examiner—Corrine Maglione
Attorney, Agent, or Firm—Paul C. Flattery; Bradford R. L. Price; Gary W. McFarron

[57] ABSTRACT

Disclosed is an improved apparatus and method for collecting, freezing and removing a liquid such as blood or blood components, and particularly blood plasma. In accordance with the present invention, a container (16) for blood plasma is defined by a pair of substantially flat, flexible opposing sidewalls (40, 42) which are substantially adjacent when the container is empty. The sidewalls are peripherally sealed together to define an interior compartment, and the side seals (44, 46) converge toward one end (48) of the container. After a selected quantity of plasma is collected in the container, the filled container is formed and frozen in a wedge-shaped configuration, with the opposed sidewalls (40,42) converging toward the end of the container. An air space (82) may be provided in the top of the container so that a knife (86) may be easily inserted into the frozen container without contacting the frozen liquid (88) therein. Slight warming of the container then permits the frozen contents to be removed efficiently as a single slug. Also disclosed is a form (60) for shaping a container as described above into a wedge-shape for freezing. The form includes a pair of rigid, perforated walls (62, 66) hinged together at one end (64) and configured to receive a container therebetween. The rigid walls of the form are disposed to shape the container walls into a converging configuration during freezing.

18 Claims, 3 Drawing Sheets

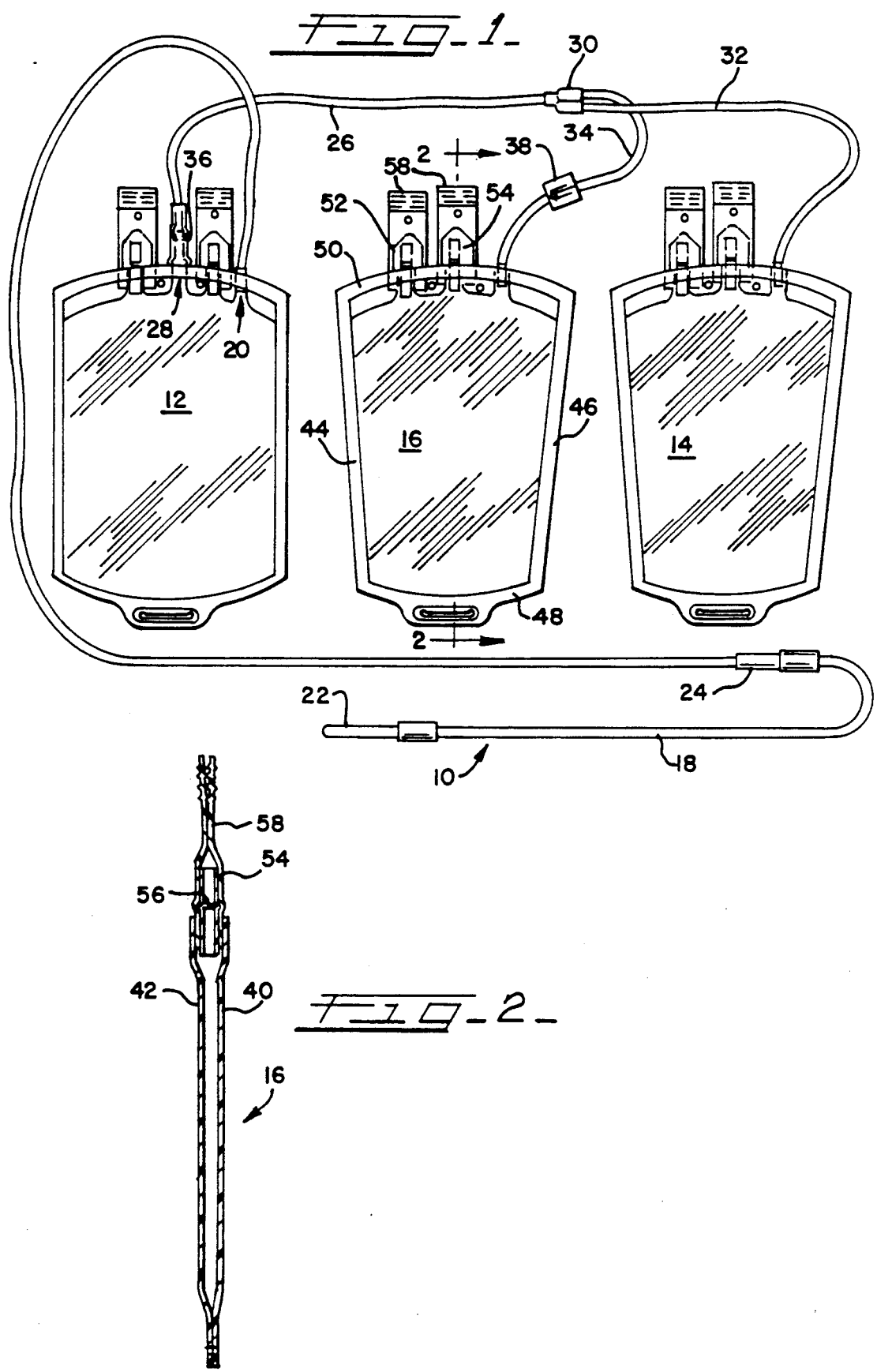

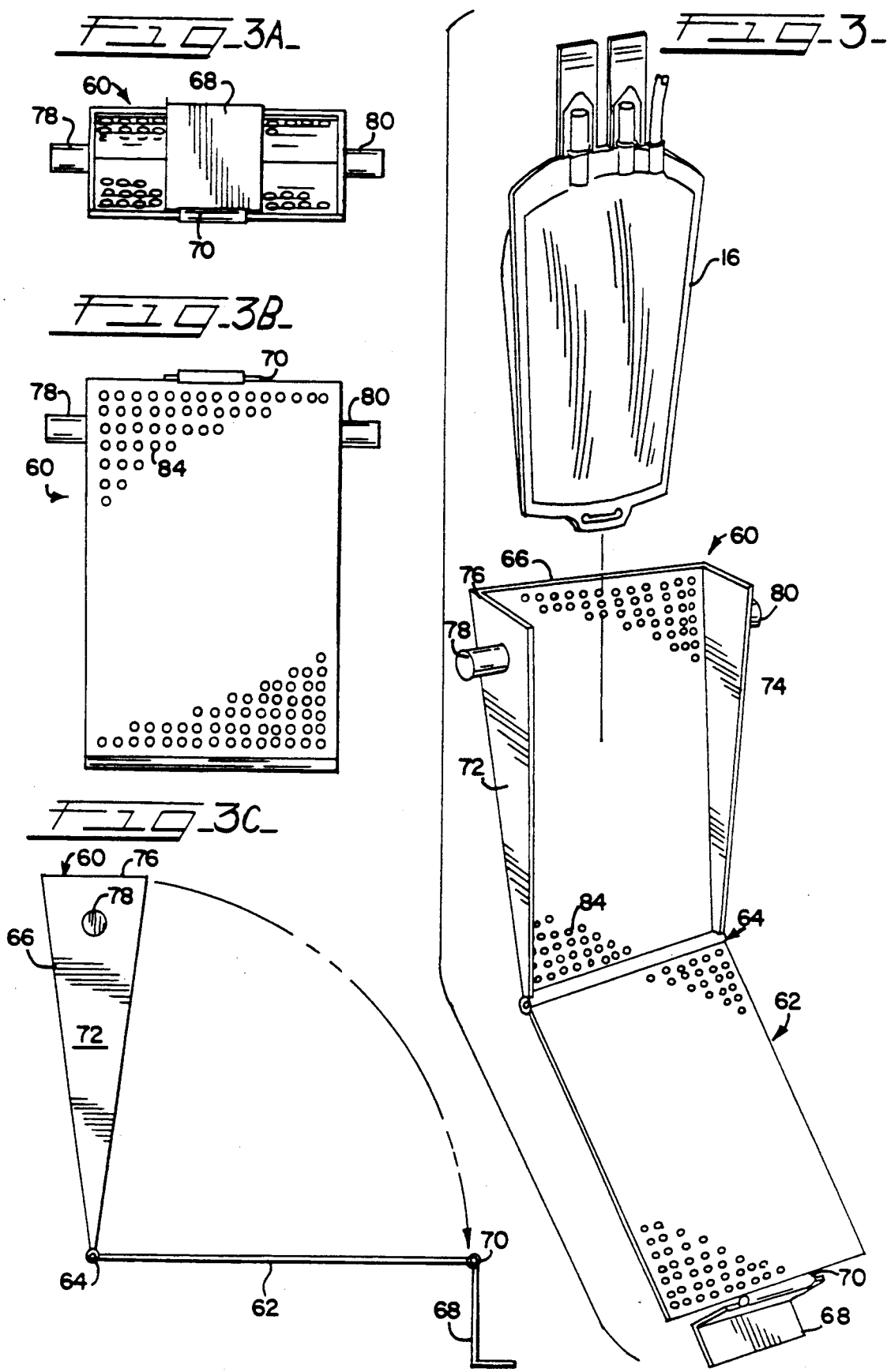

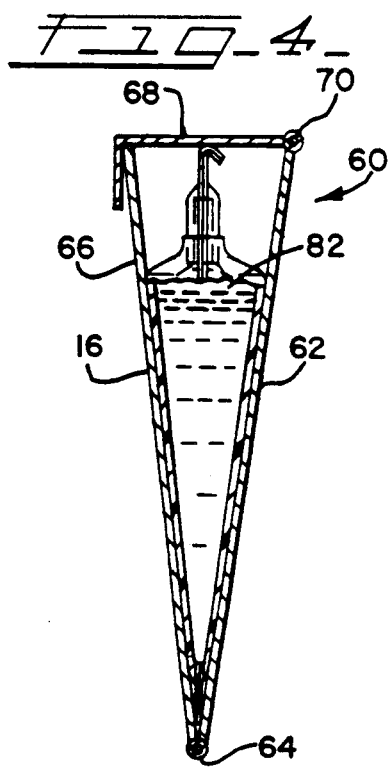
FIG-4-
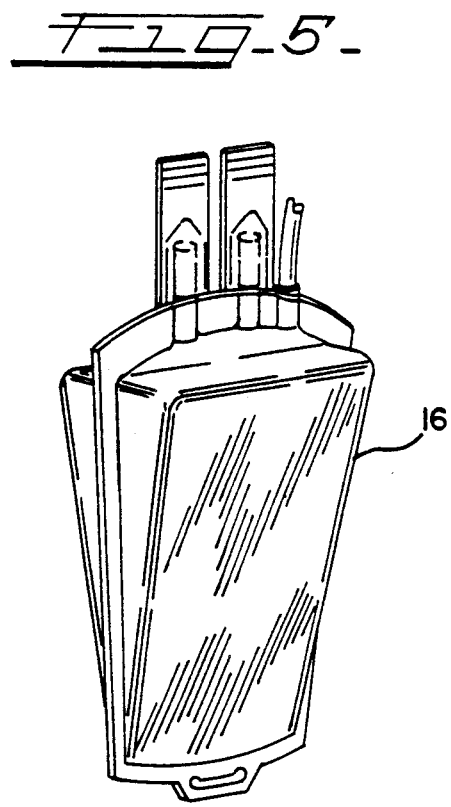
FIG-5-
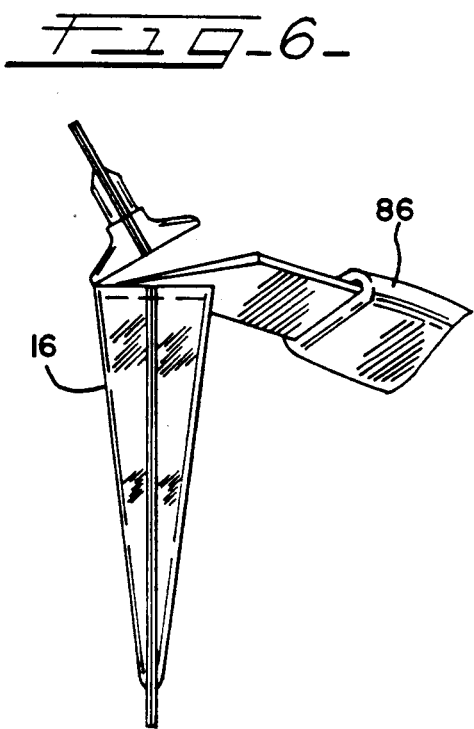
FIG-6-
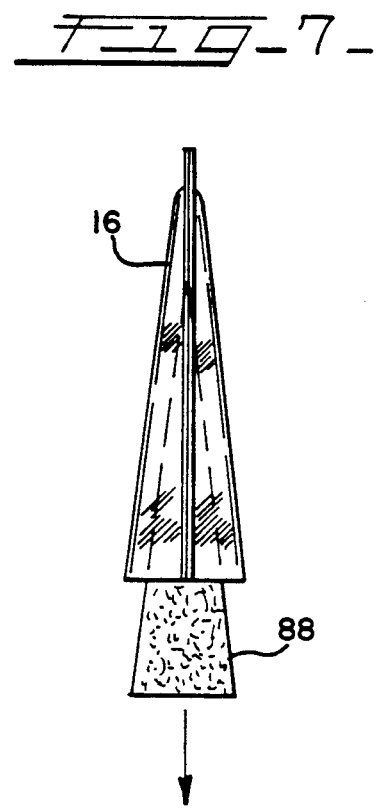
FIG-7-

APPARATUS AND METHOD FOR COLLECTING AND FREEZING BLOOD PLASMA

BACKGROUND OF THE INVENTION

The present invention relates to an apparatus and method for storing and freezing a liquid. More particularly, the present invention relates to an apparatus and method for collecting, storing, freezing and removing a frozen liquid from a plastic container, wherein the liquid is generally blood plasma.

Blood plasma is usually obtained through volunteer donation. In general, the blood is collected from the donor, processed into its component parts, including plasma, and frozen or stored for future infusion or further fractionation.

To this end, blood may be collected from the donor into an interconnected multiple-bag collection system, such as that marketed by the Fenwal Division of Baxter Healthcare, Inc., of Deerfield, Ill., U.S.A., under product code number 4R1402. In such a system, whole blood from the donor is first collected into a donor bag. The donor bag is then centrifuged to separate the whole blood into two layers: a lower layer of red cells and an upper layer of plasma. The plasma contains platelets, which are instrumental in the clotting process. This plasma is commonly referred to as platelet-rich plasma. The platelet-rich plasma is expressed, usually by manually squeezing the donor bag, into a second bag of the multiple-bag blood collection system.

If there are three bags in the blood collection system, as there are in the above-identified Baxter Healthcare product, the third bag may contain a red blood cell preservative to extend the shelf-life of the red blood cells. The red blood cell preservation solution is transferred to the donor bag and mixed with the packed red blood cells. The tube between the donor bag and the rest of the blood collection system is then sealed and severed.

To further separate the platelet rich plasma into platelets and plasma, the bag containing the platelet rich plasma is again centrifuged. This forms a lower layer of platelets and an upper layer of platelet-poor plasma. The platelet-poor plasma is then expressed into the third bag of the blood collection system and the tube connecting these two bags is sealed and severed.

Following collection and fractionation, some blood components are usually frozen for increased storage life and for ease of transportation to another location. The bags containing the platelet-poor plasma, for example, are typically placed into blast freezers designed for quickly freezing liquids. The frozen plasma is then stored in a storage freezer.

The frozen plasma can be thawed and used for plasma infusion or processed by further fractionation into its component parts, such as serum albumen, antihemophilic factor, fibrinogen, gamma globulin and the like. As a first step in plasma fractionation, the frozen plasma must be removed from the bag. As a result of the soft and pliable nature of vinyl at room temperature, the shape of the vinyl collection bags and the freezing process itself, the plasma tends to freeze in a large bulbous lump in the bottom of the bag. This makes simple removal of the frozen plasma slug very difficult and time consuming. In one removal technique, the blood collection bags are immersed in liquid nitrogen to make the plasma and the bag colder, and thus more brittle. The collection bags are then manually beaten onto a table to fracture the bags. The large chunks of frozen plasma are manually selected from among the broken pieces of vinyl bag material. However, any plasma stuck to a blood collection bag or trapped in a corner, fold, or wrinkle of the bag is swept from the table with the waste. As a result, a significant quantity of the collected plasma also may be wasted in this procedure.

One form of apparatus and method to improve recovery of frozen plasma is described in U.S. Pat. No. 4,253,458. This patent discloses a bag for collection of plasma which is made of a polyolefin material, which material is significantly stiffer than vinyl and generally maintains its as-molded shape. The shape of the polyolefin bag is configured wherein the sides taper substantially from the top towards the bottom, so that the frozen slug of plasma may be more completely expelled from the bag. Although the polyolefin bag improves the efficiency of plasma removal, because it is more rigid than vinyl, it does not provide a lay-flat configuration when empty. Accordingly, fewer containers can be packaged in a given sized shipping container. Moreover, polyolefin containers are considerably more expensive than vinyl, due to material costs and to the blow molding process used to make such containers.

U.S. Pat. No. 4,340,152 discloses a method and apparatus for removing frozen blood automatically from containers such as the container disclosed in U.S. Pat. No. 4,253,458, discussed above. That patent does not, however, address the increased cost of polyolefin containers or the higher shipping cost associated with such containers.

Accordingly, it is a general object of this invention to provide an improved apparatus and method useful for the collection of blood and blood components.

It is a more particular object of this invention to provide an apparatus and method useful in the collection of blood and blood components in vinyl bags.

These and other objects of the present invention are set forth in the following detailed description of the illustrated embodiment of the present invention.

SUMMARY OF THE INVENTION

The present invention is directed to an improved apparatus and method for collecting, freezing and removing a liquid such as blood or blood components, and particularly blood plasma. In accordance with the present invention, a container for blood plasma is defined by a pair of substantially flat, flexible opposing sidewalls which are substantially adjacent when the container is empty. The sidewalls are peripherally sealed together to define an interior compartment, and the side seals converge toward one end of the container. After a selected quantity of plasma is collected in the container, the filled container is formed and frozen in a wedge-shaped configuration, with the opposed sidewalls converging toward the end of the container. An air space may be provided in the top of the container so that a knife or other cutting means may be easily inserted into the frozen container without contacting the frozen liquid therein. Slight warming of the container then permits the frozen contents to be removed efficiently as a single slug.

In accordance with the present invention, a form is also provided for shaping a container as described above into a wedge-shape for freezing. The form includes a pair of rigid, perforated walls hinged together at one end and configured to receive a container therebetween. The rigid walls of the form are disposed to shape the container walls into a converging configuration during freezing.

Additional features and advantages of the present invention will be apparent from the detailed description of the presently preferred embodiments and from the drawings.

DESCRIPTION OF THE DRAWINGS

FIG. 1 is a plan view of an interconnected, sealed, multiple bag blood collection system in accordance with this invention;

FIG. 2 is a cross-sectional view of a blood plasma bag in accordance with this invention, taken along line 2—2 of FIG. 1;

FIG. 3 is a perspective view of a plasma bag embodying the present invention being inserted into a form embodying the present invention, for freezing;

FIG. 3A is a top view of the form of FIG. 3 in the closed position;

FIG. 3B is a front elevation view of the form of FIG. 3;

FIG. 3C is a side view of the form of FIG. 3, with the cover shown in the open position;

FIG. 4 is a cross-sectional view of the bag and form of FIG. 3 in assembled condition taken substantially from the left side;

FIG. 5 is a perspective view of a wedge-shaped frozen plasma bag embodying the present invention with plasma therein;

FIG. 6 is a side view of a plasma bag embodying the present invention being cut open; and FIG. 7 is a side view of a plasma bag after it has been cut open, showing the frozen plasma slug being expelled.

DETAILED DESCRIPTION OF THE PREFERRED EMBODIMENT

The invention, together with the objects and advantages thereof may best be understood by making reference to the following description, taken in conjunction with the accompanying drawings; the several figures of which like reference characters identify identical elements.

Referring to FIG. 1, the present invention, for purposes of illustration only, may be generally embodied in the interconnected, sealed multiple blood bag collection system 10 and in the method and apparatus for collecting, freezing and moving a frozen liquid such as blood plasma. Of course, the present invention is not limited to the collection and storage of blood plasma, and the scope of the invention is set forth in the appended claims.

The depicted blood collection system 10 includes a donor bag 12, a platelet bag 14 and a plasma bag 16. For receiving whole blood into the donor bag, the system 10 includes blood colleCtion tubing 18 which communicates with the interior of the donor bag 12 through port 20. The tubing 18 terminates in a blood collection needle 22, shown with its cover on, and includes a blood sampling port 24, all of well-known construction. For transferring blood components from one bag to another, the system 10 may also include tubing 26, which extends from a second port 28 of the donor bag to a Y-fitting 30. Additional tubing segments 32 and 34 extend from the Y-fitting 34 to the plasma and platelet bags 14 and 16, respectively.

In brief, the system 10 may be used with blood collection and fractionation as follows. After whole blood is collected in the donor bag 12, the donor bag 12 and its contents are centrifuged at 1100×g to separate the whole blood into two layers: a lower layer of packed red cells and an upper layer of platelet-containing plasma. The donor bag is then manually manipulated as by squeezing to express the platelet rich plasma into platelet bag 14. For isolating the platelet and plasma bags until access is required, a valve means such as a frangible cannula 36 may be provided in the outlet from the donor bag 12. More particularly, the frangible cannula 36 may be of the design depicted in U.S. Pat. Nos. 4,181,140 or 4,299,247, and openable by external manipulation of the tubing 26 to fracture the cannula and allow flow through tube 26.

Following transfer of the platelet-rich plasma, the tube 26 may be sealed and severed. In a two-bag system, platelet-rich plasma in the platelet bag 14 could be frozen, as described below. In a three bag system, as shown at 10, additional steps may be carried out. For example, it may be desirable to add a preservative to the red blood cells remaining in the donor bag 12. In a three bag blood collection system, such as is shown at 10, the plasma bag 16 may contain a quantity of a red blood cell preservation fluid, such as ADSOL Preservation solution, manufactured by Fenwal Laboratories Division of Baxter Healthcare, Inc. of Deerfield, Ill., U.S.A., 60015, or its equivalent.

The red blood cell preservation solution in the plasma bag 16 can be manually expressed into the tube 34 through a valve means 38 and into the donor bag 12. The valve means 38 may be similar in configuration to the frangible cannula 36. The tube 26 is then sealed and cut, and donor bag 12 is stored and used as needed.

Once the platelet rich plasma has been transferred to the platelet bag 14 and the donor bag is severed, the platelet bag 14 is then centrifuged to make a lower layer of platelet concentrate and an upper layer of platelet-poor plasma. The platelet-poor plasma is transferred via the tube 32, the connector 30 and the tube 34 into the now empty plasma bag 16. Tubes 32 and 34 are then sealed, and the two bags 14 and 16 are severed for their various uses.

One or more bags of a blood collection system, such as shown at 10, may be configured according to this invention. Either bag 14 or 16 or both may be configured according to the present invention. As best seen in FIGS. 1 and 2, according to the present invention, the plasma bag 16 comprises a pair of substantially flat, flexible, opposing sidewalls 40, 42, preferably made of a vinyl material such as polyvinyl chloride, although other materials may also be used without departing from the present invention. The sidewalls 40 and 42 are substantially adjacent when the bag 16 is in an unfilled condition, so that the bag 16 is in a lay-flat configuration when empty. This lay-flat configuration provides an easily packaged blood collection system 10, which takes up little storage space before use.

The sidewalls 40 and 42 of the plasma bag 16 are sealed together around the entire periphery at side seams 44 and 46, bottom seam 48, and top seam 50, to define an interior compartment. The seams can be of any conventional sealing method appropriate to the material chosen. For bags made of vinyl material such as polyvinyl chloride, the sidewalls may simply be heat sealed together along the edge seams.

To enhance the ability to remove frozen plasma or the like from the container, the side seams 44 and 46 of the plasma bag 16 converge from the top seam 50 towards the bottom seam 48. In the preferred embodiment, the side seams converge continuously from the top seam 50 towards the bottom seam 48, although other arrangements such as a step-wise converging shape may also be used.

The plasma bag 16 has in this embodiment a capacity of approximately 300 ml. In the preferred embodiment, however, the plasma bag 16 will not be filled in its entirety. Instead, it will be filled to approximately 250 ml. with approximately 30–35 cc of air. The air space allows for expansion while the contents are freezing. Furthermore, and importantly, after the contents are frozen, the air space permits a cutting means to cut the top off of the transfer bag without contacting the contents, as will be discussed below.

In this embodiment, the plasma bag 16 is provided with two plastic port tubes 52, 54 for accessing the interior, as is well known in the art. The port tubes 52 and 54 are sealed adhesively or thermally between the sidewalls 40 and 42. As best seen in FIG. 2, the port tubes 52 and 54 contain an intermediate, frangible membrane 56 which seals the port tubes 52 and 54 until such time as the seal is manually broken. The port tubes 52 and 54 are covered by port protectors, such as peel-apart tabs 58, which normally seal the port tubes 52 and 54 and keep them sterile, until access to the interior of bag 16 is required for infusion, for example.

The platelet-poor plasma in plasma bag 16 may be used for a subsequent infusion or processed into other blood fractions. In any event, it is typically frozen to increase its useful life. In accordance with the present invention, the plasma bag 16 is preferably placed into a form as shown generally at 60, for freezing. The form 60 shapes the container to provide a configuration which is more conducive for extraction of the frozen plasma, and which is less likely to cause plasma-trapping tucks and folds in the frozen transfer bag.

Turning now to FIGS. 3 to 3C, the form 60 according to the present invention is shown. As best seen in FIG. 3, the form 60 of this invention has a cover portion 62 hinged at 64 to a back portion 66. The cover 62 is pivotal in relation to the back 66 between a first or open position, as seen in FIGS. 3 and 3c, and a second or closed position, as seen in FIGS. 3a and 3b. In the open position the form 60 can receive one or more plasma bags 16 between the cover 62 and the back 66. In the closed position, the form 60 encloses the plasma bag 16, and the form 60 engages the sidewalls and presses them into a V-shape.

An L-shaped latch 68 is provided in order to hold the cover 62 and the back 66 together during the molding and freezing process. The latch 68 is pivotally mounted at hinge 70 and movable to a latched position as seen in FIGS. 3a, 3b and 4, where it engages over the top edge of the back portion 66.

When contained within the form 60, plasma bag 16 and thus the liquid inside are formed into a wedge-shape. The sides 72 and 74 of the form are triangular converging from a top side 76 of the form 60 preferably continuously down towards the hinge 64 as shown in FIG. 3c, of the preferred embodiment. Other geometric configurations will be in keeping with this invention, as long as the sides converge, so that the top is basically wider and thicker than the bottom.

After a filled plasma bag 16 is placed within the form 60, the form is suspended by hangers 78 and 80 within a blast freezer unit (not shown). In the preferred embodiment, the hangers are oppositely extending rods, although other configurations of hangers will work in conjunction with this invention. Blast freezer units for this purpose are well-known in the art.

FIG. 4 shows a cross-sectional view of the form 60 and plasma bag 16 cut away to show the liquid inside, during the freezing process. An air space 82 is left at the top of the plasma bag 16 when it is filled with liquid, to facilitate opening of the plasma bag 16 at the manufacturing site, discussed below in connection with FIG. 6, and to permit expansion of the liquid during the freezing process.

To promote freezing, the form 60 is constructed of a thermally conductive material, such as stainless steel, aluminum or the like. Furthermore, the cover 62 and the back 66 of the form 60 are ventilated with perforation holes 84 to promote cold air circulation and thus freezing. The perforations 84 in the preferred embodiment are an evenly spaced matrix, with the number of perforations depending on the size, application, desired freezing time and the like.

After freezing, the frozen plasma bag 16, will have substantially the conformation seen in FIG. 5. If the contents of the plasma bag 16 are to be removed from the transfer bag in the frozen state, for example, for further processing, the plasma bag 16 must be opened. To accomplish this, the top of the plasma bag 16 is completely removed, as by a knife 86 illustrated in FIG. 6. The removal process may be manual or automatic. In either case, the presence of the air space 82 in the top of the plasma bag 16 allows the top to be removed without contacting the frozen plasma.

The surface of the plasma bag 16 is then, in the preferred embodiment, warmed by quickly heating the surface with warm water, steam, or electro-magnetic radiation, as is known in the art. This warming releases the frozen plasma slug from container wall, and the frozen plasma slug 88 can be simply and quickly removed in a single piece by inverting the bag, as shown in FIG. 7. The removal process may be manual or automatic. For example, the frozen slug 88 could also be forced out by two counter rotating rollers or other devices, as shown in U.S. Pat. No. 4,253,458, FIG. 4 and corresponding text.

It should be understood that various changes and modifications to the presently preferred embodiments described herein will be apparent to those skilled in the art. Such changes and modifications can be made without departing from the spirit and scope of the present invention and without diminishing its attendant advantages. The above has been offered for illustrative purposes only, and is not intended to limit the invention of this application, which is defined in the claims below.

What is claimed is:

1. A container having a frozen plasma slug therein, comprising:
    a pair of sidewalls made from polyvinyl chloride material, peripherally sealed together to define an interior compartment;
    means for accessing the interior compartment;
    said sidewalls converging toward one end of said container to form a generally wedge-shape;
    a quantity of frozen plasma within said container;
    wherein said container of frozen plasma is formed by providing a container of flexible opposing sidewalls having an empty lay-flat configuration, collecting a quantity of liquid plasma in said container, inserting the liquid plasma-containing container into a form that defines a V-shape about the container, engaging the sidewalls of the plasma-containing counter with the form so as to press the sidewalls into a V-shape, so that said sidewalls converge toward one end of the container, and freezing the plasma-containing container while maintaining the container in said V-shaped configuration in the form, thereby forming a wedge-shaped container having a frozen, wedge-shaped plasma slug therein.

2. A container in accordance with claim 1 wherein said quantity of frozen liquid is of a selected volume so that a portion of the interior compartment between the frozen liquid and the other end remains unfilled.

3. A container in accordance with claim 1 wherein said sidewalls converge continuously toward said one end when said container is filled with said frozen liquid.

4. A container in accordance with claim 1 wherein said sidewalls are rigid when said container is filled with said frozen liquid.

5. A container in accordance with claim 1 wherein said side seals converge toward said one end of said container.

6. A container in accordance with claim 1 wherein said means for accessing said interior compartment further comprises at least one tubular inlet at the other end.

7. A container in accordance with claim 6 further comprising flexible tubing communicating with said tubular inlet.

8. A container in accordance with claim 1 wherein said plasma is substantially free of platelets.

9. A method for collecting and freezing plasma comprising:
   providing a container comprising a pair of substantially flat flexible opposing plastic sidewalls, which sidewalls are substantially adjacent when the container is in an unfilled condition so as to provide an empty lay-flat configuration; said sidewalls being peripherally sealed together to define an interior compartment; and means for accessing said interior compartment;
   collecting a quantity of liquid plasma in said container, said liquid plasma resulting in a generally bulbous shape in the sidewalls of the container;
   inserting the liquid plasma-containing container into a form that defines a V-shape about the container;
   engaging the sidewalls of the plasma-containing container with the form so as to press the sidewalls into a V-shape, so that said sidewalls converge toward one end of the container; and
   freezing the plasma-containing container while maintaining the container in said V-shaped configuration in the form, thereby forming a wedge-shaped container having a frozen, wedge-shaped plasma slug therein.

10. A method in accordance with claim 9 further comprising the step of placing the wedge-shaped container in a freezer.

11. A method in accordance with claim 9 further comprising thawing the outer layer of said frozen liquid.

12. A method in accordance with claim 9 wherein method further comprises removing the other end of said container.

13. A method in accordance with claim 12 wherein method further comprises expelling said frozen liquid out said cut end.

14. A method in accordance with claim 12 wherein said removing step comprises cutting said other end of said container without contacting the frozen liquid.

15. A form for shaping a container of liquid plasma having flexible walls, wherein the container when empty has a generally lay-flat configuration, into a generally wedge-shaped container with a frozen, generally wedge-shaped plasma slug therein, which form comprises:
   a pair of thermally-conductive rigid walls hinged together at one end;
   at least one of said rigid walls defining perforation holes to promote cold air circulation and freezing;
   said walls being relatively pivotal between a first position in which the walls are spaced sufficiently far apart to receive at least one container therebetween, and a second position sufficiently close together to engage the flexible walls of the container; and
   means for holding said rigid walls in said second position;
   said rigid walls of said form being disposed to shape the container walls into a converging configuration when moved to said second position.

16. A form in accordance with claim 15 further comprising means for hanging said form.

17. A form in accordance with claim 16 wherein said hanging means comprises oppositely extending rods.

18. A form in accordance with claim 15 wherein said holding means comprises a latch for holding said rigid walls in said second position.

* * * * *